United States Patent
Dobrozsi et al.

(10) Patent No.: US 7,138,133 B2
(45) Date of Patent: Nov. 21, 2006

(54) ORALLY ADMINISTERED LIQUID COMPOSITIONS

(75) Inventors: Douglas Joseph Dobrozsi, Loveland, OH (US); Jerry William Hayes, II, Cincinnati, OH (US); Francis Joseph David Bealin-Kelly, Walton on Thames (GB); Jayant Eknath Khanolkar, Surbition (GB); Benoit Maurice Mullet, Ashtead (GB); Shane Michael DE LA Harpe, Woking (GB); Brian James Robbins, Staines (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/974,347

(22) Filed: Oct. 10, 2001

(65) Prior Publication Data

US 2003/0113377 A1    Jun. 19, 2003

(51) Int. Cl.
*A61K 9/10* (2006.01)
*A61K 47/34* (2006.01)

(52) U.S. Cl. .................. 424/439; 424/400; 514/975; 514/850

(58) Field of Classification Search ............. 424/439, 424/400; 514/975, 850
See application file for complete search history.

(56) References Cited

U.S. PATENT DOCUMENTS

| | | | |
|---|---|---|---|
| 4,100,271 A | 7/1978 | Krezanoski | |
| 4,188,373 A | 2/1980 | Krezanoski | |
| 4,474,752 A | 10/1984 | Haslam et al. | |
| 4,474,753 A | 10/1984 | Haslam et al. | |
| 4,478,822 A | 10/1984 | Haslam et al. | |
| 4,511,563 A | 4/1985 | Schmolka | |
| 4,673,679 A | 6/1987 | Aungst et al. | |
| 4,810,503 A | 3/1989 | Carson et al. | |
| 4,849,418 A | 7/1989 | Lohner et al. | |
| 4,911,926 A | 3/1990 | Henry et al. | |
| 5,030,448 A | 7/1991 | Hunter | |
| 5,071,644 A | 12/1991 | Viegas et al. | |
| 5,100,898 A | 3/1992 | Sorrentino | |
| 5,135,751 A | 8/1992 | Henry et al. | |
| 5,141,961 A | 8/1992 | Coapman | |
| 5,143,731 A | 9/1992 | Viegas et al. | |
| 5,183,669 A * | 2/1993 | Hori | |
| 5,256,396 A | 10/1993 | Piechota, Jr. | |
| 5,292,516 A | 3/1994 | Viegas et al. | |
| 5,298,260 A | 3/1994 | Viegas et al. | |

(Continued)

FOREIGN PATENT DOCUMENTS

CA    2238409 A1    6/1997

(Continued)

OTHER PUBLICATIONS

Weinberg et al., "Sublingual Absorption of Selected Opioid Analgesics", *Clin Pharmacol Ther*, vol. 44, No. 3, 1988, pp. 335-342.

(Continued)

*Primary Examiner*—Edward J. Webman
(74) *Attorney, Agent, or Firm*—Kristin Kohler; Cynthia L. Clay; Kelly L. McDow-Dunham

(57) ABSTRACT

The present invention is an orally administered liquid pharmaceutical composition that demonstrates excellent physical stability while delivering concentrated levels of the pharmaceutical active(s). Specifically, these compositions for extended periods do not allow the active to precipitate or settle out of solution. Among the advantages of this invention is that the compositions do not require agitation/shaking prior to use as a method to re-suspend or dissolve active drug material to insure even and consistent dosing.

13 Claims, 1 Drawing Sheet

U.S. PATENT DOCUMENTS

| | | | |
|---|---|---|---|
| 5,300,295 | A | 4/1994 | Viegas et al. |
| 5,306,501 | A | 4/1994 | Viegas et al. |
| 5,318,780 | A | 6/1994 | Viegas et al. |
| 5,346,703 | A | 9/1994 | Viegas et al. |
| 5,360,615 | A | 11/1994 | Yu et al. |
| 5,366,735 | A | 11/1994 | Henry |
| 5,505,961 | A | 4/1996 | Shelley et al. |
| 5,510,389 | A | 4/1996 | Dhabhar |
| 5,527,832 | A | 6/1996 | Chi et al. |
| 5,587,175 | A | 12/1996 | Viegas et al. |
| 5,681,576 | A | 10/1997 | Henry |
| 5,731,007 | A | 3/1998 | Chung et al. |
| 5,820,854 | A | 10/1998 | Glandorf |
| 5,869,082 | A | 2/1999 | Dugger, III |
| 5,932,589 | A | 8/1999 | Galli Angeli |
| 5,955,098 | A | 9/1999 | Dugger, III |
| 6,110,486 | A | 8/2000 | Dugger, III |
| 6,290,986 | B1 * | 9/2001 | Murdoch et al. |

FOREIGN PATENT DOCUMENTS

| | | |
|---|---|---|
| EP | 0211601 A2 | 2/1987 |
| EP | 0386960 A2 | 3/1990 |
| EP | 0439335 A1 | 7/1991 |
| EP | 0551626 A1 | 7/1993 |
| WO | WO 96/29986 A1 | 10/1996 |
| WO | WO 97/10849 A1 | 3/1997 |
| WO | WO 97/21441 A1 | 6/1997 |
| WO | WO 97/38662 A2 | 10/1997 |
| WO | WO 97/39742 A1 | 10/1997 |
| WO | WO 98/06438 A2 | 2/1998 |
| WO | WO 98/29127 A1 | 7/1998 |
| WO | WO 99/16417 A1 | 4/1999 |
| WO | WO 99/32152 A2 | 7/1999 |
| WO | WO 00/21510 A2 | 4/2000 |
| WO | WO 00/41693 A2 | 7/2000 |
| WO | WO 01/19329 A2 | 3/2001 |

OTHER PUBLICATIONS

Harris et al., "Drug Delivery Via the Mucous Membranes of the Oral Cavity", *J. of Pharm Sciences*, vol. 81, No. 1, 1992, pp. 1-10.

Salomonowitz et al., "Hydrophilic-Lipophilic Balance as Predictor of Mucus Coating with Barium Sulfate" *Gastrointest Radio*, vol. 11, 1986, pp. 93-96.

Chen-Chow et al., "In Vitro Release of Lidocaine From Pluronic F-127 Gels", *International Journal of Pharmaceutics*, vol. 8, 1981, pp. 89-99.

Nurnberg et al., "Poloxamere-was ist das? Eigenschaften und Anwendungsmoglichkeiten", *Deutsche Apotheker Zeitung*, vol. 129, No. 41, 1989, pp. 2183-2187.

Reeve, "The Poloxamers: Their Chemistry and Medical Applications", *Handbook of Biodegreadable Polymers*, Editors: A. J. Domb, J. Kost and D. M. Wiseman, Harwood Acaemic Publishers, Chapter 12, pp. 231-249.

Juhasz et al., "Adhesion of Ploxamer 407 Formulations on Dog Ileal in Vitro", *Eur J Pharm Biopharm*, vol. 37, No. 4, 1991, pp. 262-265.

Pandit et al., "Cosolvent Effects on the Gel Formation and Gel Melting Transitions of Pluronic F127 Gels", *Pharmaceutical Development and Technology*, vol. 2, No. 2, 1997, pp. 181-184.

Gilbert et al., "Drug release from Pluronic F-127 gels", *International Journal of Pharmaceutics*, vol. 32, 1986, pp. 223-228.

Lenaerts et al., "Temperature-dependent rheological behavior of Pluronic F-127 aqueouos solutions", *International Journal of Pharmaceutics*, vol. 39, 1987, pp. 121-127.

Suh et al., "Pharmacokinetic and Local Tissue Disposition Studies of Naproxen Following Topical and Systemic Administration in Dogs and Rats", *Biopharmaceutics & Drug Disposition*, vol. 18, No. 7, pp. 1997, 623-633.

Cappel et al., "Effect of nonionic surfactants on transdermal drug delivery: II. Poloxamer and poloxamine surfactants", *International Journal of Pharmaceutics*, vol. 69, 1991, pp. 155-167.

Viegas et al., "Osmotic behavior of poloxamer 407 and other non-ionic surfactants in aqueous solutions" *International Journal of Pharmaceutics*, vol. 160, 1998, pp. 157-162.

Lu et al., "Diffusion studies of methotrexate in Carbopol and Poloxamer gels", *International Journal of Pharmaceutics*, vol. 160, 1998, pp. 1-9.

Jewell et al., "Pharmacokinetics of RheothRx Injection in Healthy Male Volunteers", *Journal of Pharmaceutical Sciences*, vol. 86, No. 7, 1997, pp. 808-812.

Bochot et al., "Liposomes Dispersed Within a Thermosensitive Gel: A new Dosage Form for Ocular Delivery of Oligonucleotides", *Pharmaceutical Research*, vol. 15, No. 9, 1998, pp. 1364-1369.

Edsman et al., "Rheological evaluation of poloxamer as an in situ gel for ophthalmic use", *European Journal of Pharmaceutical Sciences*, vol. 6, 1998, pp. 105-112.

Kim et al., "Trials of in situ-gelling and mucoadhesive acetaminophen liquid suppository in human subjects", *International Journal of Pharmaceutics*, vol. 174, 1998, pp. 201-207.

Brown et al., "Thermorheology of polaxamer 407: effect of alcohols and drugs", *J. Pharm. Pharmacol.*, vol. 50, Supplement: pp. 159.

Gaisford et al., "Temperature induced aggregation in aqueouos solution of a series of PEO-PPO-PEO copolymers", *International Journal of Pharmaceutics*, vol. 174, 1998, pp. 39-46.

Wang et al., "Kinetics of Sol-to-Gel Transition for Poloxamer Polyols", *Journal of Applied Polymer Science*, vol. 43, 1991, pp. 283-292.

Stratton et al., "Drug Delivery Matrix Containing Native Protein Precipitates Suspended in a Poloxamer Gel", *Journal of Pharmaceutical Sciences*, vol. 86, No. 9, 1997, pp. 1006-1010.

* cited by examiner

ORALLY ADMINISTERED LIQUID COMPOSITIONS

TECHNICAL FIELD

The present invention is in the field orally administered liquid compositions for delivering pharmaceutical actives to humans and animals.

BACKGROUND

Pharmaceutical actives are generally delivered using dosage forms designed to promote ease in using while encouraging maximum efficacy of the active. Among the challenges regarding creating dosage forms taken by mouth is formulating such a product in a form small enough to be easily swallowed.

When the desired dosage form is a liquid, then the pharmaceutical actives or actives must be solubilized in a vehicle wherein the composition is easy to use and maximizes therapeutic effectiveness. One such composition is a pharmaceutical suspension. A suspension is where solid active particles are dispersed within a liquid vehicle. Although suspensions are a very useful way to concentrate an active in a small volume, they possess some inherent disadvantages. One disadvantage is that over time the active particles settle to the bottom or float to the top of the liquid, resulting in a suspension that is not homogenous. Thus, a patient who uses a suspension in such a condition is likely to receive more or less active than the intended dose. In some cases this could result in a consumer taking a high and potentially a hazardous dose or conversely, a dose that lacks the minimum level of active required to provide the intended therapeutic benefit. Another disadvantage of suspensions relates to absorption of the active. For absorption to take place, a pharmaceutical active must first be in a solubilized state. Thus, suspensions that contain actives not previously solubilized must undergo dissolution in bodily fluids prior to absorption. Such a dissolution step may slow down the onset of the desired therapeutic effect.

In light of the disadvantages of suspensions mentioned above, those skilled in the art have created solutions in the form of elixirs and syrups for delivery of actives. These solutions can be easily and conveniently swallowed in 5, 10 or even 50 ml volumes. In certain cases, however, it is desirable to deliver the active in a true solution that is in a small volume of less than about 3 ml, even less than 1 ml. Up to now, achieving such small volumes has been problematic and for some actives nearly impossible. The problem is exacerbated where the dose level of the active is required to be large, or wherein the active agent is especially insoluble in the usual vehicles used for pharmaceuticals.

Liquid-filled, soft gelatin capsules were developed in response to this challenge. There are, however, limits to using such capsules. One limitation is when the requisite level of actives cannot be contained in a small volume. Liquid-centered, soft gelatin capsules containing acetaminophen has been the subject of a great deal of effort in order to solve problems such as those mentioned above. For example, in U.S. Pat. No. 5,505,961, assigned to R. P. Scherer reputes to have solved such problems associated with soft gelatin capsules, particularly where high dose levels of acetaminophen is required to provide therapeutic benefits. It is disclosed therein that acetaminophen, with or without other actives, is soluble in solvents including polyethylene glycol, water, propylene glycol, a solubilizing agent including potassium (or sodium) acetate and polyvinylpyrrolidone or PVP. It is disclosed therein, PVP is essential for inhibiting crystallization in such compositions. PCT Application WO 93/00072, Coapman, discloses a process for solubilizing pharmaceutical actives considered difficult to solubilize. This process requires PVP to aid in solubilizing the active agent and preventing precipitation. Similar limitation are disclosed for the acetaminophen solutions described in PCT Application WO 95/23595, by Dhabhar, wherein PVP is disclosed as an essential component of the compositions that are the subject matter of the patent.

PVP is a high molecular weight polymer that while inhibiting crystallization, also is responsible for increasing compositional viscosity of the liquid compositions. Such a viscosity increase is not significant for products contained in capsules intended for swallowing. The high viscosity associated with such liquid compositions containing PVP, however, does inhibit effective oral dosing of low volume products particularly from exact dosing implements such as medicine droppers, oral syringes, dosing cups and sachets. High viscosity liquid compositions are an impediment to being easily dosed from these types of exact dosing implements and do not spread easily over large surface areas of oral mucosal tissue.

When avoiding PVP and its related problems, new problems associated with oral dosing can develop. For example, U.S. Pat. No. 5,360,615, assigned to R. P. Scherer, discloses solubilizing the active by adding acid or base to cause the partial ionization of the active. It has been found, however, that this approach is undesirable in the case of liquid solutions to be delivered into the mouth for absorption through mucosal membranes since the active's ionization inhibits such absorption.

One very important consideration in choosing a product form, therefore, is determining the active's intended delivery site within the body. The prior art describing medicaments to be delivered to the stomach include liquid-center gelatin capsules. The liquids contained in these capsules are not intended to contact the body until the gelatin shell dissolves in the stomach. In such a product it is superfluous whether the liquid in the gelatin is highly viscous, or even a paste or solid. For administration into the mouth, however, the composition's ability to flow is critical. Low viscosity liquids permit accurate administration from current or developing exacting dispensing or dosing devices for administering a liquid composition to a person. Low viscosity liquids are easier to swallow and make the composition acceptably palatable. Such consumer acceptance is very important for encouraging consumers to comply with dosing instructions to receive the intended therapeutic benefit. Aside from the aesthetic considerations, it's desired that the formulation spread over a large surface area of mucosal tissue to enhance the diffusion of the respective actives within the formulation through the mucosal membranes.

SUMMARY OF THE INVENTION

The inventors here have worked to create compositions comprising pharmaceutical actives normally difficult to solubilize in high concentration for delivery into the mouth. The fundamental relationship between the pharmaceutical actives and the vehicles into which they are incorporated is that the actives are maintained in solution while the in-use character of the composition is flowable as well as a pourable for enhancing the delivery of the pharmaceutical actives to the oral cavity.

After diligent research in trying to obtain such compositions, the inventors have surprisingly discovered that there is an important relationship of the components comprising the vehicle for solubilizing the active. When the components of the vehicle are in the particular levels and ratios to one another as shown in FIG. 1, the pharmaceutical actives remain in solution and are pourable and flowable at temperatures other than ambient temperature such as body temperature.

The present invention, therefore, is an orally administered liquid pharmaceutical composition that demonstrates excellent physical stability while delivering concentrated levels of the pharmaceutical active(s). Specifically, these compositions do not exhibit active precipitation from the solution for extended periods. Other advantages of this invention include uniform and correct dosing to patients. Additionally, the compositions remain liquid in the oral cavity thereby exposing large surface areas of oral mucosal tissue to the pharmaceutical actives intended to pass through that oral mucosal tissue. As a result, the compositions are efficacious and patient-preferable due to their improved palatability. The formulations also permit the solubilization of both lipophilic active agents, and hydrophilic excipients and formulation aids at the same time.

DEFINITIONS

Figure 1:
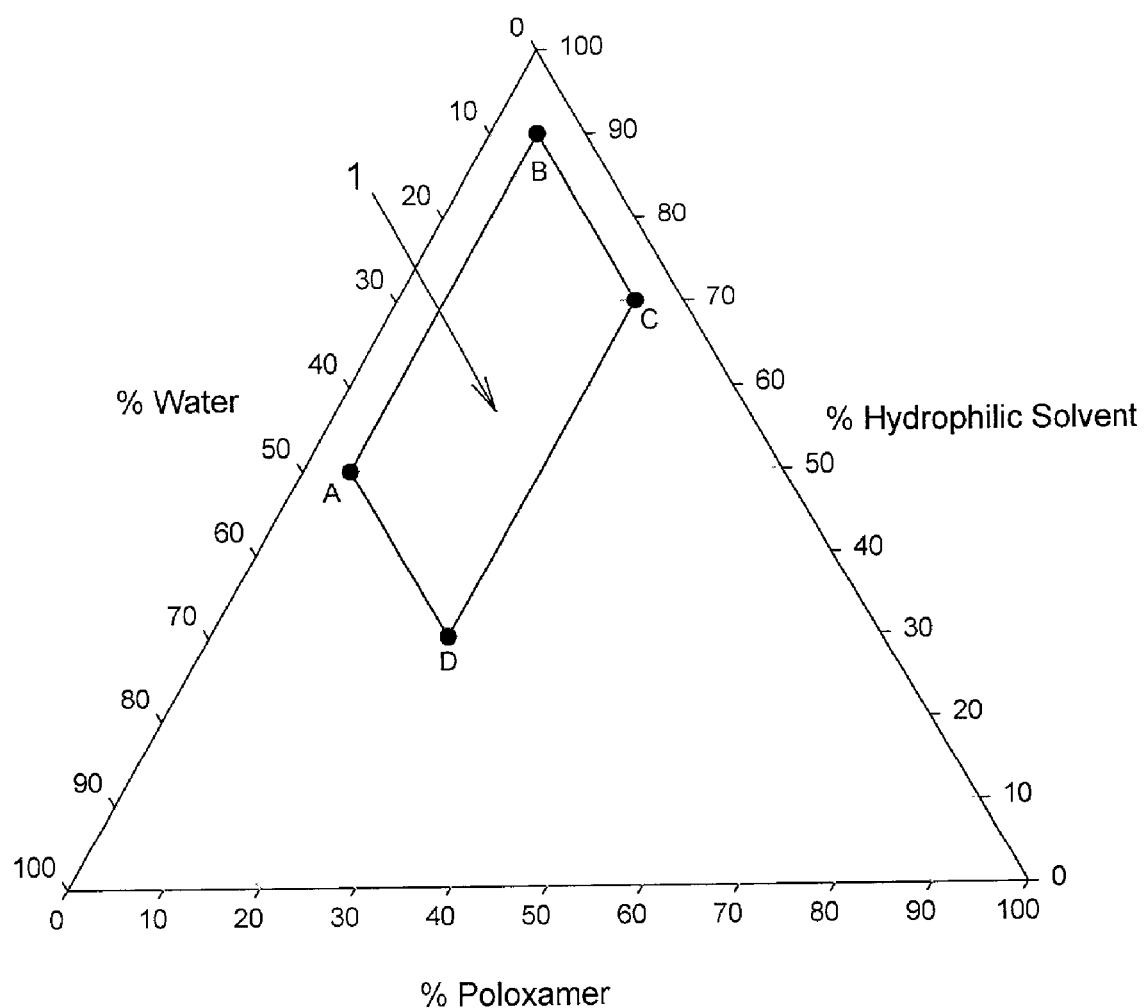
FIG. 1 illustrates a ternary mixture diagram that is a graphical representation of three varying relationships of the three primary components of the vehicle of compositions of the present invention. The axes of the diagram correspond to these three components.

Terms useful herein are defined below. Additionally, terms used in the art, as well as general concepts, are further described in Schramm, *The Language of Colloid and Interface Science*, American Chemical Society, (1993), incorporated herein by reference:

"Hydrophilic solvents" are used herein to describe polar, pharmaceutically acceptable solvents that are miscible with water and possess a dielectric constant ($\epsilon$) of approximately 20 or greater as found in Martin's Physical Pharmacy, Fourth Edition, Pages 213–214.

"Low volume dose" as used herein means doses of a liquid composition less than about 3 mls wherein the pharmaceutical active is sufficiently concentrated to produce the desired therapeutic response upon oral administration.

"Optical density" or "OD" is a measurement of the absorption of radiation by a mixture of ingredients forming a liquid or a layer of said liquid. The OD is expressed mathematically as the negative common logarithm of the transmittance of light (T) by the mixture. Optical density value is measured using the equation, $OD = \log_{10}(1/T)$.

"Orally administered" as used herein means the composition is introduced into the oral cavity making contact with the tissues inside the oral cavity prior to it being swallowed or ingested.

"Physical stability" as used herein in the context of the present composition means the composition's resistance to changes in the number and relative amounts of phases of matter present.

"Pourable" as used herein means the ability of a liquid to remain in a highly flowable state regardless of the exposure of said liquid to temperatures from about 15° C. to about 40° C. at normal atmospheric pressure.

"Solution" as used herein means a uniform dispersed mixture at molecular or ionic level of one or more pharmaceutical actives (the solute) in one or more other substances (the solvent). The physical state of the solution at normal ambient conditions is such that it is readily dispensed from a vessel by pouring.

DETAILED DESCRIPTION OF THE INVENTION

The present invention is an orally administered liquid pharmaceutical composition having excellent physical stability while containing concentrated levels of pharmaceutical actives. In addition to these pharmaceutical actives, these compositions comprise a vehicle for solubilizing the actives wherein the vehicle comprises hydrophilic solvents, polyoxyalkylene block copolymers and water together in levels and ratios to one another wherein the actives are solubilized and remain as such over extended periods of time. Hydrophilic solvents and water also facilitate the incorporation of other compounds, such as sweetening agents and stabilizers, into the composition of the present invention. Compositions of the present invention provide accurate delivery of the active, particularly when the composition is packaged in exacting dose measuring devices including graduated tubes, droppers, pipettes, single or unit dose liquid elixir packages, atomizers, liquid filled edible capsules or drops or other such packages. In addition, these solutions readily spread over large surface areas of the mucosal tissues in the oral cavity, throat, oropharynx and combinations thereof, resulting in some actives being rapidly absorbed.

Consumers show strong preference for lower dose volumes that contain a sufficiently high enough concentration of pharmaceutical actives to provide the desired therapeutic benefit of the active. As a result of this effort to meet consumer needs, the compositions of the present invention are intended to be dosed in low volumes. In the present invention it is envisioned that the maximum volume of a single dose of the compositions of the present invention is no greater that about 3 ml, alternatively no greater than 2.5 ml.

All percentages of the components comprising the invention are herein referred to by their weight of the composition.

Pharmaceutical Actives

The pharmaceutical actives of the present invention are those that are particularly difficult to solubilize in a small volumes of solvents since the actives are already close to their solubility limit. At such concentrations these pharmaceutical actives tend to be physically unstable, precipitating out of solution when the composition is subject to minor changes in ambient temperature, level of contaminates in the solution or other commonly known factors that precipitate an active from a solution. Precipitation can take place at any point from just after manufacture and packaging of the compositions, through its normally expected shelf life.

The compositions of the present invention contain pharmaceutical actives that are soluble in the polyoxyalkylene block copolymers, hydrophilic solvents and water that comprise the vehicle of the composition of the present invention. The pharmaceutical actives include guaifenesin alone or in combination other actives selected from the group of antihistamines, antitussives, expectorants/mucolytics, bronchodilators, decongestants and mixtures thereof.

Guaifenesin is known for symptomatic relief of respiratory conditions characterised by dry, non-productive cough and presence of mucus in the respiratory tract. The action of guaifenesin ameliorates dry unproductive cough by decreasing sputum viscosity and difficulty in expectoration and increasing sputum volume. (Ref. Remington The Science and Practice of Pharmacy, 20 Third Ed., p.1303, published by Philadelphia College of Pharmacy and Sciences; herein incorporated by reference). Additionally, it is indicated as a fertility aid in women by thinning mucous endogenous to the reproductive tract.

There are a host of actives that may be combined with guaifenesin. These actives are from suitable classes of agents including, but not limited to the following:

Antihistamines: including, hydroxyzine, pyrilamine, phenindamine, dexchlorpheniramine, clemastine diphenhydramine, azelastine, acrivastine, levocarbastine, mequitazine, astemizole, ebastine, loratadine, cetirizine, terfenadine, promethazine, dimenhydrinate, meclizine, tripelennamine, carbinoxamine, cyproheptadine, azatadine, brompheniramine, triprolidine, cyclizine, thonzylamine, pheniramine, and mixtures thereof.

Antitussives: including, hydrocodone, noscapine, benzonatate, diphenhydramine, chlophedianol, clobutinol, fominoben, glaucine, pholcodine, zipeprol, hydromorphone, carbetapentane, caramiphen, levopropoxyphene, codeine, dextromethorphan, pholcodine and mixtures thereof.

Expectorants/Mucolytics: including, ambroxol, bromhexine, terpin, potassium iodide, n-acetylcysteine, and mixtures thereof.

Bronchodilators: preferably for inhalation, including, albuterol, epinephrine, ephedrine, metaproterenol, terbutaline, theophylline, aminphylline isoetharine, terbutaline, isoetharine, pirbuterol, bitolterol, fenoterol, rimeterol, ipratroprium, and mixtures thereof.

Decongestants: including pseudoephedrine, phenylephrine, phenylpropanolamine and their salts and mixtures thereof.

The level of pharmaceutical actives in the compositions of the present invention is from about 2% to about 40%, alternatively 3% to 40%, and also 5% to 30% of the composition. The level of each active making up the aggregate or combination of the pharmaceutical actives is determinable by one skilled in the art when considering factors including the physicochemical and bioavailability characteristics of the active, the dose regime and the age, weight and physical condition of the patient as well as the stability of the system that incorporates these actives. In regard to this last point, the inventors spent significant effort in working within the confines of present composition's components to determine whether such a system will remains physically stable.

Vehicle

In addition to the actives discussed above, the composition of the present invention comprises a vehicle. The level of the vehicle can be 100% of the composition minus the active and optional ingredients as discussed below. In the present invention, the level of the vehicle in the composition is typically from about 40% to about 98%, alternatively from about 60% to about 90%. The vehicle of the present inventions comprises a three-component mixture of (a) polyoxyalkylene block copolymers, (b) hydrophilic solvents and (c) water, wherein these three components are present in specific proportions to each other. The specific proportions are most readily represented using the ternary (or 3 component) mixture diagram. Such diagrams are well known in the art to described such mixtures; see "Experiments with Mixtures", John A. Cornell, 1990, John Wiley and Sons, New York, pp. 2–8; herein incorporated by reference. In the case of such mixtures, the total amount of the three components present represents 100% of the vehicle and each component is a proportion of that total amount. The vehicle of the compositions of the present invention may be described precisely using the three-component mixture diagram referred to here as FIG. 1. The vehicle is defined as region 1 of FIG. 1, bounded by the lines connecting the vertices of the parallelogram A, B, C and D or segment lines AB, BC, CD and DA.

These vertices are located on the diagram wherein the polyoxyalkylene block copolymer proportions of the is 5% and 25% of the vehicle, hydrophilic solvent portion at 30, 50, 70 and 90% of the vehicle, and water at a portion of 5% and 45% of the vehicle. The vertices of the parallelogram are found at the following 4 points:

| | Component | | | |
|---|---|---|---|---|
| Point | polyoxyalkylene block copolymer | hydrophilic solvent | water | Total of the Components |
| A | 5 | 50 | 45 | 100 |
| B | 5 | 90 | 5 | 100 |
| C | 25 | 70 | 5 | 100 |
| D | 25 | 30 | 45 | 100 |

In determining the percentages of each component comprising the vehicle, the components cannot be varied independently of each other. The proportion of one component depends on the proportion of the other two. For example, if the water proportion falls within the range of 5–45% and the polyoxyalkylene block copolymer falls within the range of 5–25%, the hydrophilic solvent range is determined using the following equation:

100%−(% polyoxyalkylene block copolymer+% water);

In this example, the range is calculated to be from about 30% to about 90%.

Polyoxyalkylene block copolymers, also herein referred to as "poloxamers", are nonionic block copolymers of ethylene oxide and propylene oxide corresponding to the following structure:

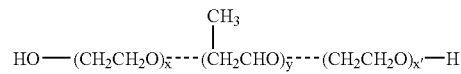

The polyoxyalkylene block copolymers useful in the present invention include those wherein x has a value from about 1 to about 130, y has a value from about 1 to about 72 and x has a value from about 0 to about 130, wherein the average molecular weight of said copolymer is from about 3000 to about 15,000. Alternatively, the polyoxyalkylene block copolymers of the present invention are those where x equals 100, y equals 70 and x' equals 100 and has an average molecular weight of about 12,600 alternatively where x equals 76, y equals 31 and x' equals 76 and has an average molecular weight of 8400. The vehicle of the present invention comprises from about 5% to about 25% and alternatively from about 5% to about 20% poloxamer.

The poly (oxyethylene) segment is hydrophilic and the poly (oxypropylene) segment is hydrophobic. Families of poloxamers are available and vary in the number of blocks, the overall average molecular weight, and in the percentage of the molecule which is hydrophilic. A block refers to a single polyoxyethylene or polyoxypropylene segment. Di-block and tri-block polymers have been described. In the case of tri-block copolymers, the blocks can be arranged in the format of one polyoxypropylene block surrounded by 2 polyoxyethylene blocks, that being the most common poloxamer structure, or alternatively as one polyoxyethylene block surrounded by 2 polyoxypropylene blocks, the latter sometimes referred to as a reverse poloxamer. Poloxamers are available under the trade names of Lutrol®, Monolan®, or Pluronic®. The chemical structure, synthesis, and properties have been described as [poly (ethylene oxide)/poly (propylene oxide)] block copolymer surfactants by Paschalis Alexandridis, *Current Opinions in Colloid and Interface Science*, Vol. 2, pp. 478–489 (1997); herein incorporated by reference.

For health care applications preferable poloxamers include Pluronic® F127, Pluronic® L1220, and Pluronic® F68. These specific polymers are available from BASF Corporation.

In the present invention it is envisioned that combining hydrophilic solvents with the poloxamers and water provides an environment suitable for solubilizing pharmaceutical actives wherein the composition demonstrates the previously discussed physical stability. The vehicle of the present invention comprises from about 30% to about 90%, alternatively from about from about 35% to about 90% and finally from about 40% to about 90% hydrophilic solvents.

The hydrophilic solvents of specific interest are selected from the group consisting of monohydric and polyhydric alcohols. The preferable monohydric alcohols of the present invention include ethanol and tetraglycol. Absolute ethanol is available from Aaper Alcohol & Chemical Co., Shelbyville, Ky. Polyhydric alcohols of the present invention are selected from the group consisting of glycols, monosaccharides, oligosaccharides and mixtures thereof. Glycols are particularly useful as the hydrophilic solvent of the present invention. Glycols used in the present invention are selected from the group consisting of glycerin, propylene glycol and polyethylene glycol. The monosaccharides of the present invention are selected from the group consisting glyceraldehydes, ribose, glucose, fructose, invert sugars (such as honey) and mixtures thereof. The oligosaccharides of the present invention are selected from the group consisting of maltose, sucrose, raffinose, lactose, cellobiose, ribose, sorbitol, mannitol, xylitol, inositol, galactose, mannose, xylose, rhamnose, glutaraldehyde and mixtures thereof.

In addition to the components previously discussed, the present invention comprises water. The level of water in the vehicle of the present invention is from about 5% to about 45%, alternatively from about 5% to about 40%.

Optional Ingredients

The composition can include optional ingredients traditionally included in orally administered liquid compositions, typically to improve the aesthetics of the composition. These optional ingredients include, but are not limited to, dyes, fragrances, preservatives, antioxidants, and similar types of compounds. Specific optional ingredients include, but, are not restricted to surfactants including tyloxapol, polysorbate 80, lauroglycol 90, polyox 40 stearate, capryol 90, polymers including polyvinylpyrrolidone, hydroxypropyl methyl cellulose, beta-cyclodextrins, or solvents, such as propylene carbonate, n-methylpyrrolidone, transcutol, dimethylisosorbide and mixtures thereof. These optional ingredients are included in the composition in an amount sufficient to perform their intended function without compromising the benefits associated with the present invention.

METHODS

Methods for Treating Illness

The delivery of drugs into the bloodstream by placing a dosage form into the mouth can be classified into two major subclasses dependant upon the desired action. In one case where the drug is delivered into the blood by absorption after swallowing (i.e. from the stomach, small intestine or colon) and in the other case where absorption, or at least the significant amount of the absorption occurs through the membranes of the oral cavity either immediately or over extended periods of time when the compositions are retained in the mouth prior to swallowing. This route is generally referred to as "buccal" or "oral mucosal" absorption versus the former route normally referred to as peroral administration of actives. Peroral administration of actives is by far the most commonly used in all of medicine, has been well studied, and is explained in detail in: Mayerson, M., Principles of Drug Absorption; Chapter 2 in "Modem Pharmaceutics", $2^{nd}$ ed., G. S. Banker and C. T. Rhodes, editors, Marcel Dekker Inc., New York, 1990; herein incorporated by reference.

In terms of the methods of delivery of the active, it is generally accepted that oral mucosal delivery inside the mouth is targeted to the sub-lingual region to achieve rapid therapeutic effects; see D. Harris and J. R. Robinson, *Drug Delivery via the Mucus Membranes of the Oral Cavity*, Journal of Pharmaceutical Sciences 81: 1, 1992. Such dosage forms are delivered under the tongue, on the floor of the mouth, and held there for some extended time. The inventors have found, however, that a large increase in bioavailability with very rapid absorption can be achieved for particular pharmaceutical actives when the subject compositions are placed against any of the mucosal membranes of the mouth, throat, tongue, oropharynx and combinations thereof and swallowed; see PCT Publication 00/41693, Dobrozsi et al., published Jul. 20, 2000; herein incorporated by references.

The form of the invention is a liquid or an elixir intended to be applied to any of the mucosal membranes within the mouth. This can be achieved using a medicine dropper that is calibrated to indicate the proper amount to be administered, and squirting the elixir onto the tongue prior to swallowing. The elixir can be atomized into mouth and throat and then swallowed. It can be encapsulated into some sort of edible and, or chewable shell that makes it portable and convenient to transport and administer without having to measure the quantity of liquid elixir. Examples of encapsulation shells include hard candies as are used for lozenges, gelatin and starch-based shells and combination thereof. The elixir may be packaged into single dose, small, disposable vials easily opened wherein the elixir is squirted or poured into the mouth. Typical dosage forms of the composition of the present invention contain no more than about 3 ml., alternatively from about 0.2 ml. to about 3ml.

Method for Characterizing the Physical Stability of the Present Invention

Susceptibility of changes in morphology and appearance of a composition is indicative of the composition's physical stability. Among the tests to measure this stability is that of measuring the liquid's optical density. This method is thermo-chemical, wherein samples of the compositions and control samples are prepared by the methods as disclosed in the examples below, and packed in 30 ml amber glass bottles leaving a minimal headspace. The bottles were placed in a thermally insulated chamber at a constant temperature of less than 5° C. until being pulled for testing. The OD of the samples including controls and samples of the present invention are evaluated for physical stability by measuring the optical density of each sample. The test is made using a spectrophotometer such as a Jenway Model 6405 UV/VIS, set at a transmittance wavelength of 530 nm. Physical stability is a function of the composition's transmittance of light. The light transmittance of the composition is directly related to the liquids turbidity, sedimentation/precipitation and, or content of crystals found in the liquid.

Measurements of the samples are made at intervals of 7 days. The values are averaged over the entire testing period of 3 months. A formulation with lower optical density values is proposed as having greater overall physical stability. It is required for the composition of the present invention to have Optical Density (OD) value less or equal to 0.05, indicating good physical stability of the composition.

EXAMPLES

Example 1

Composition for the Treatment of Cough with an Expectorant

| Component | % (w/w) |
| --- | --- |
| Guaifenesin | 15.39 |
| Dextromethorphan Base | 1.13 |
| Propylene Glycol | 41.32 |
| Water | 20.38 |
| Alcohol, 96% v/v | 10.65 |
| Poloxamer[1] | 7.01 |
| Sucralose | 1.40 |
| Flavor | 1.50 |
| Sodium Saccharin | 0.40 |
| Acesulfame | 0.40 |
| Sodium Metabisulfite | 0.20 |
| Disodium EDTA | 0.20 |
| Monoammonium Glycyrrizinate | 0.02 |

[1]Pluronic ® F127 is available from BASF Specialty Chemicals, Mt. Olive, NJ.

Preparation:

Add propylene glycol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base and monoammonium glycyrrizinate and mix until uniform. In another vessel (water pre-mix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform Subsequently, add desired flavor component and mix until uniform.

Example 2

Composition for the Treatment of Cough with an Expectorant

| Component | % (w/w) |
| --- | --- |
| Guaifenesin | 15.39 |
| Dextromethorphan Base | 1.13 |
| Propylene Glycol | 25.77 |
| Poloxamer[1] | 15.00 |
| Water | 13.59 |
| Alcohol, (100%) | 10.00 |
| Transcutol | 10.00 |
| Tyloxapol | 5.00 |
| Sucralose | 1.40 |
| Flavor | 1.50 |
| Sodium Saccharin | 0.40 |
| Acesulfame | 0.40 |
| Sodium Metabisulfite | 0.20 |
| Disodium EDTA | 0.20 |
| Monoammonium Glycyrrizinate | 0.02 |

[1]Pluronic ® F127 is available from BASF Specialty Chemicals, Mt. Olive, NJ.

Preparation:

Add propylene glycol, tyloxapol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base, transcutol and monoammonium glycyrrhizinate and mix until uniform. In another vessel (water pre-mix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, desired flavor component and mix until uniform.

Example 3

Composition for the Treatment of Cough with an Expectorant

| Component | % (w/w) |
| --- | --- |
| Guaifenesin | 15.39 |
| Dextromethorphan Base | 1.13 |
| Poloxamer[1] | 15.56 |
| Water | 20.81 |
| Propylene Glycol | 34.24 |
| Alcohol, 96% v/v | 10.65 |
| Sucralose | 0.40 |
| Flavor | 1.12 |
| Sodium Saccharin | 0.20 |
| Acesulfame | 0.10 |
| Sodium Metabisulfite | 0.20 |
| Disodium EDTA | 0.20 |

[1]Pluronic ® F68 is available from BASF Specialty Chemicals, Mt. Olive, NJ.

Preparation:

Add propylene glycol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base and mix until uniform. In another vessel (water pre-mix), add water, EDTA, sodium saccharin, acesulfame, sucralose and sodium metabisulfite. Mix until all materials are dissolved.

Add the water containing premix to the main mixing vessel containing the poloxamer. Mix until uniform. While stirring cool and add the alcohol containing premix to the main vessel and continue to mix until uniform Subsequently, add desired flavor component and mix until uniform.

Example 4

Composition for the Treatment of Cough with an Expectorant

| Component | % (w/w) |
|---|---|
| Guaifenesin | 15.40 |
| Dextromethorphan Base | 1.13 |
| Propylene Glycol | 27.74 |
| Poloxamer[1] | 18.52 |
| Water | 18.09 |
| Alcohol, (100%) | 10.00 |
| Tyloxapol | 5.00 |
| Sucralose | 1.40 |
| Flavor | 1.50 |
| Sodium Saccharin | 0.40 |
| Acesulfame | 0.40 |
| Sodium Metabisulfite | 0.20 |
| Disodium EDTA | 0.20 |
| Monoammonium Glycyrrizinate | 0.02 |

[1]Pluronic ® F127 is available from BASF Specialty Chemicals, Mt. Olive, NJ.

Preparation:

Add propylene glycol, tyloxapol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base, and monoammonium glycyrrizinate and mix until uniform. In another vessel (water pre-mix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, desired flavor component and mix until uniform.

Example 5

Composition for the Treatment of Cough with an Expectorant

| Component | % (w/w) |
|---|---|
| Guaifenesin | 15.40 |
| Dextromethorphan Base | 1.13 |
| Propylene Glycol | 29.67 |
| Water | 17.81 |
| Poloxamer[1] | 11.87 |
| Alcohol, (100%) | 10.00 |
| Transcutol | 10.00 |
| Sucralose | 1.40 |
| Flavor | 1.50 |
| Sodium Saccharin | 0.40 |
| Acesulfame | 0.40 |
| Sodium Metabisulfite | 0.20 |
| Disodium EDTA | 0.20 |
| Monoammonium Glycyrrizinate | 0.02 |

[1]Pluronic ® F127 is available from BASF Specialty Chemicals, Mt. Olive, NJ.

Preparation:

Add propylene glycol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base, transcutol and monoammonium glycyrrizinate and mix until uniform. In another vessel (water pre-mix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, desired flavor component and mix until uniform.

Example 6

Composition for the Treatment of Cough with an Expectorant

| Component | % (w/w) |
|---|---|
| Guaifenesin | 15.39 |
| Dextromethorphan Base | 1.13 |
| Propylene Glycol | 52.82 |
| Water | 20.38 |
| Alcohol, (96% v/v) | 0.44 |
| Poloxamer[1] | 7.01 |
| Sucralose | 0.40 |
| Flavorants | 1.12 |
| Sodium Saccharin | 0.10 |
| Acesulfame | 0.10 |
| Sodium Metabisulfite | 0.20 |
| Disodium EDTA | 0.91 |

[1]Pluronic ® L1220 is available from BASF Specialty Chemicals, Mt. Olive, NJ.

Preparation:

Add propylene glycol and poloxamer to a clean vessel (main mix). While stirring, heat the mixture as appropriate to sufficiently dissolve the poloxamer. Add Guaifenesin and continue stirring. Once a uniform solution is obtained remove from heat source and continue mixing. In a separate vessel (alcohol pre-mix) add alcohol, dextromethorphan base, and mix until uniform. In another vessel (water premix), add water, EDTA, sodium saccharin, acesulfame, sucralose and sodium metabisulfite. Mix until all materials are dissolved.

Add the water containing premix to the main mixing vessel containing the poloxamer. Mix until uniform. While stirring cool and add the alcohol containing premix to the main vessel and continue to mix until uniform Subsequently, add desired flavor component and mix until uniform.

Example 7

Composition for the Treatment of Cough with an Expectorant

| Component | % (w/w) |
|---|---|
| Guaifenesin | 15.38 |
| Dextromethorphan Base | 1.12 |
| Poloxamer[1] | 14.00 |
| Propylene Glycol | 30.00 |
| Water | 17.00 |
| Alcohol, (96% v/v) | 10.00 |
| Transcutol | 10.00 |
| Flavorants | 1.00 |
| Sucralose | 0.90 |
| Sodium Saccharin | 0.20 |
| Acesulfame | 0.20 |
| Sodium Metabisulfite | 0.10 |
| Disodium EDTA | 0.10 |

[1]Pluronic ® F127 is available from BASF Specialty Chemicals, Mt. Olive, NJ.

Preparation:

Add propylene glycol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base, transcutol and mix until uniform. In another vessel (water pre-mix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, desired flavor component and mix until uniform.

Example 8

Composition for the Treatment of Cough with an Expectorant

| Component | % (w/w) |
|---|---|
| Guaifenesin | 15.39 |
| Dextromethorphan Base | 1.13 |
| Tetraglycol | 25.25 |
| Propylene Glycol | 20.21 |
| Poloxamer[1] | 14.03 |
| Water | 10.00 |
| Alcohol, (96% v/v) | 10.65 |
| Sucralose | 1.40 |
| Sodium Saccharin | 0.44 |
| Acesulfame | 0.40 |
| Sodium Metabisulfite | 0.10 |
| Disodium EDTA | 0.10 |
| Flavorants | 0.90 |

[1]Pluronic ® F127 is available from BASF Specialty Chemicals, Mt. Olive, NJ.

Preparation:

Add propylene glycol, tetraglycol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base and mix until uniform. In another vessel (water pre-mix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, desired flavor component and mix until uniform.

Example 9

Composition for the Treatment of Cough with an Expectorant

| Component | % (w/w) |
|---|---|
| Guaifenesin | 25.00 |
| Dextromethorphan Base | 1.83 |
| Poloxamer[1] | 16.36 |
| Water | 20.50 |
| Propylene Glycol | 24.34 |
| Alcohol, 96% v/v | 10.65 |
| Sucralose | 0.40 |
| Flavor | 0.40 |
| Sodium Saccharin | 0.20 |
| Acesulfame | 0.20 |
| Sodium Metabisulfite | 0.10 |
| Disodium EDTA | 0.02 |

[1]Pluronic ® F68 is available from BASF Specialty Chemicals, Mt. Olive, NJ.

Preparation:

Add propylene glycol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base and mix until uniform. In another vessel (water premix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform Subsequently, add desired flavor component and mix until uniform.

Example 10

Composition for the Treatment of Cough with an Expectorant

| Component | % (w/w) |
| --- | --- |
| Guaifenesin | 20.00 |
| Dextromethorphan Base | 1.47 |
| Propylene Glycol | 19.75 |
| Poloxamer[1] | 16.07 |
| Water | 13.59 |
| Alcohol, (100%) | 10.00 |
| Transcutol | 10.00 |
| Tetraglycol | 5.00 |
| Sucralose | 1.40 |
| Flavor | 1.52 |
| Sodium Saccharin | 0.40 |
| Acesulfame | 0.40 |
| Sodium Metabisulfite | 0.20 |
| Disodium EDTA | 0.20 |

[1]Pluronic ® F127 is available from BASF Specialty Chemicals, Mt. Olive, NJ.

Preparation:

Add propylene glycol, tetraglycol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. In a separate vessel (alcohol pre-mix) add alcohol, dextromethorphan base, and transcutol and mix until uniform. In another vessel (water pre-mix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, desired flavor component and mix until uniform.

Example 11

Composition for the Treatment of Bronchitis with an Expectorant

| Component | % (w/w) |
| --- | --- |
| Guaifenesin | 15.26 |
| Ambroxol | 2.36 |
| Propylene Glycol | 47.27 |
| Water | 17.94 |
| Alcohol, 100% | 10.00 |
| Poloxamer[1] | 7.17 |

[1]Pluronic ® F127 is available from BASF Specialty Chemicals, Mt. Olive, NJ.

Preparation:

Add propylene glycol and poloxamer to a clean vessel (main mix). While stirring, heat the mixture as appropriate to sufficiently melt the poloxamer. While stirring add guaifenesin and ambroxol. Once a uniform solution is obtained remove from heat source and continue mixing. Finally, add alcohol and water to the vessel and mix until uniform.

Example 12

Liquid Cough Lozenges

| Material | % (w/w) |
| --- | --- |
| Dextromethorphan Base | 2.05 |
| Guaifenesin | 20.00 |
| Poloxamer[1] | 15.50 |
| Propylene Glycol | 46.71 |
| Water | 13.44 |
| Alcohol, (96% v/v) | 0.40 |
| Sucralose | 0.40 |
| Sodium Saccharin | 0.15 |
| Acesulfame | 0.15 |
| Sodium Metabisulfite | 0.15 |
| Disodium EDTA | 0.15 |
| Flavorants | 0.90 |

[1]Pluronic ® L1220 is available from BASF Specialty Chemicals, Mt. Olive, NJ.

Preparation:

Add propylene glycol, and poloxamer to a clean vessel (main mix). While stirring, heat the mixture as appropriate to sufficiently melt the poloxamer. Add guaifenesin continue stirring. Once a uniform solution is obtained remove from heat source and continue mixing. In a separate vessel (alcohol pre-mix) add alcohol, dextromethorphan base and mix until uniform. In another vessel (water pre-mix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently add the desired flavor component and mix until uniform. Make individual filled lozenges containing about 1.0 ml. of liquid per lozenge by a commonly used method such as extrusion.

Example 13

Chewable Soft Gelatin Capsules

| Component | % (w/w) |
| --- | --- |
| Dextromethorphan Base | 2.05 |
| Poloxamer[1] | 12.25 |
| Propylene Glycol | 47.56 |
| Water | 10.44 |
| Alcohol, (96% v/v) | 10.46 |
| Sucralose | 0.40 |
| Sodium Saccharin | 0.10 |
| Acesulfame | 0.10 |
| Sodium Metabisulfite | 0.20 |
| Disodium EDTA | 0.15 |
| Guaifenesin | 15.39 |
| Flavorants | 0.90 |

[1]Pluronic ® F127 is available from BASF Specialty Chemicals, Mt. Olive, NJ.

Preparation:

Add propylene glycol, and poloxamer to a clean vessel (main mix). While stirring, heat the mixture as appropriate to sufficiently melt and dissolve the poloxamer. Add guaifenesin continue stirring. Once a uniform solution is obtained remove from heat source and continue mixing. In a separate vessel (alcohol pre-mix) add alcohol and dextromethorphan base and mix until uniform. In another vessel (water premix), add water, EDTA, sodium saccharin, acesulfame, sucralose and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, desired flavor component and mix until uniform. Make individual filled soft gelatin capsules containing about 1.0 ml. of liquid Example 14

Composition for the Treatment of Sinusitis or Symptoms of Allergic Rhinitis

| Component | % (w/w) |
| --- | --- |
| Guaifenesin | 15.37 |
| Bromhexine | 0.67 |
| Propylene Glycol | 48.00 |
| Water | 18.46 |
| Alcohol, 100% | 10.00 |
| Poloxamer[1] | 7.50 |

[1]Pluronic ® F127 is available from BASF Specialty Chemicals, Mt. Olive, NJ.

Preparation:

Add propylene glycol and poloxamer to a clean vessel (main mix). While stirring, heat the mixture as appropriate to sufficiently melt the poloxamer. While stirring add guaifenesin and bromhexine. Once a uniform solution is obtained remove from heat source and continue mixing. Finally, add alcohol and water to the vessel and mix until uniform.

Example 15

Composition for the Treatment of Bronchitis with Expectorant

| Component | % (w/w) |
| --- | --- |
| Guaifenesin | 15.37 |
| Bromhexine | 0.67 |
| Ambroxol | 2.30 |
| Propylene Glycol | 46.70 |
| Water | 17.46 |
| Poloxamer[1] | 7.50 |
| Alcohol, 100% | 10.00 |

[1]Pluronic ® F127 is available from BASF Specialty Chemicals, Mt. Olive, NJ.

Preparation:

Add propylene glycol and poloxamer to a clean vessel (main mix). While stirring, heat the mixture as appropriate to sufficiently melt the poloxamer. While stirring add guaifenesin, bromhexine and ambroxol. Once a uniform solution is obtained remove from heat source and continue mixing. Finally, add alcohol and water to the vessel and mix until uniform.

Example 16

Composition for the Treatment of Infertility

| Component | % (w/w) |
| --- | --- |
| Guaifenesin | 18.50 |
| Propylene Glycol | 26.75 |
| Poloxamer[1] | 19.00 |
| Water | 16.50 |
| Alcohol, (100%) | 10.00 |
| Flavorants | 1.40 |
| Tetraglycol | 5.00 |
| Sucralose | 1.20 |
| Flavor | 1.20 |
| Sodium Saccharin | 0.25 |
| Sodium Metabisulfite | 0.10 |
| Disodium EDTA | 0.10 |

[1]Pluronic ® F127 is available from BASF Specialty Chemicals, Mt. Olive, NJ.

Preparation:

Add propylene glycol, tetraglycol and poloxamer to a clean vessel (main mix). While stirring, heat the mixture as appropriate to sufficiently melt the poloxamer. Add Guaifenesin and continue stirring. Once a uniform solution is obtained remove from heat source and continue mixing. Add alcohol and continue mixing. In another vessel (water premix), add water, EDTA, sodium saccharin, sucralose and sodium metabisulfite. Mix until all materials are dissolved.

Add the alcohol containing premix to the main mixing vessel containing the poloxamer mix until uniform. While stirring, add the water containing premix to the main vessel and continue to mix until uniform. Subsequently, desired flavor component and mix until uniform.

What is claimed is:

1. A liquid composition comprising from about 2% to about 40% guaifenesin, from about 1% to about 40% dextromethorphan, and a vehicle comprising:

a. from about 5% to about 25% of a polyoxyalkylene block copolymer wherein said polyoxyallcylene block copolymer corresponds to the formula:

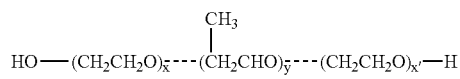

x has a value from about 1 to about 130, y has a value from about 1 to about 72 and x' has a value from 0 to about 130;

b. from about 30% to about 90% of a hydrophilic solvent; and c. from about 5% to about 45% water;

wherein the proportions of polyoxyalkylene block copolymer, hydrophilic solvent and water are such that the vehicle is in the region bounded by segment lines AB, BC, CD and DA of FIG. 1; and wherein the composition is suitable for oral administration.

2. The liquid composition according to claim 1 wherein said polyoxyalkylene block copolymer is at a level of 5% to 25%, hydrophilic solvent is at a level from about 35% to about 90% and wherein said water is at a level from about 5% to about 40% of said vehicle.

3. The liquid composition according to claim 1 wherein said polyoxyalkylene block copolymer is at a level of 5% to 20%, hydrophilic solvent is at a level from about 40% to about 90% and wherein said water is at a level from about 5% to about 40% of said vehicle.

4. A composition according to claim 1 wherein said hydrophilic solvent is selected from the group consisting of monohydric and polyhydric alcohols.

5. The orally administered composition according to claim 4 wherein said polyhydric alcohols are selected from the group consisting of glycols, monosaccharides, oligosaccharides and mixtures thereof.

6. The liquid composition according to claim 1 wherein the hydrophilic solvent is ethanol.

7. A liquid composition comprising from about 2% to about 40% guaifenesin, from about 1% to about 40% dextromethorphan, and a vehicle comprising:
   a. from about 5% to about 25% of a polyoxyalkylene block copolymer wherein said polyoxyalkylene block copolymer corresponds to the formula:

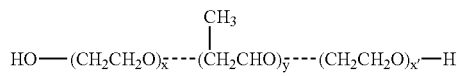

x has a value from about 100, y has a value from about 70 and x' has a value of about 100;
   b. from about 30% to about 90% of a hydrophilic solvent; and
   c. from about 5% to about 45% water;
   wherein the proportions of polyoxyallcylene block copolymer, hydrophilic solvent and water are such that the vehicle is in the region bounded by segment lines AB, BC, CD and DA of FIG. 1; and
   wherein the composition is suitable for oral administration.

8. The liquid composition according to claim 7 wherein said polyoxyalkylene block copolymer is at a level of 5% to 25%, hydrophilic solvent is at a level from about 35% to about 90% and wherein said water is at a level from about 5% to about 40% of said vehicle.

9. The liquid composition according to claim 7 wherein said polyoxyalkylene block copolymer is at a level of 5% to 20%, hydrophilic solvent is at a level from about 35% to about 90% and wherein said water is at a level from about 5% to about 40% of said vehicle.

10. A liquid composition comprising from about 5% to about 30% guaifenesin, from about 1% to about 40% dextromethorphan, and a vehicle comprising:
    a. from about 5% to about 20% of a polyoxyalkylene block copolymer wherein said polyoxyalkylene block copolyiner corresponds to the formula:

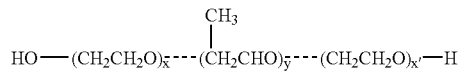

x equals 100, y equals 70 and x' equals 100 and has an average molecular weight of about 12,600;
    c. from about 40% to about 90% propylene glycol and ethanol; and
    d. from about 5% to about 40% water;
    wherein the proportions of polyoxyalkylene block copolymer, hydrophilic solvent and water are such that the vehicle is in the region bounded by segment lines AB, BC, CD and DA of FIG. 1; and
    wherein the composition is suitable for oral administration.

11. A composition according to claim 10 additionally comprising ambroxyl.

12. A composition according to claim 11 additionally comprising bromhexine.

13. A composition according to claim 10 additionally comprising ambroxyl and bromhexine.

* * * * *